Feb. 16, 1954 E. S. BOERNER Plant Pat. 1,252
ROSE PLANT
Filed Feb. 24, 1953
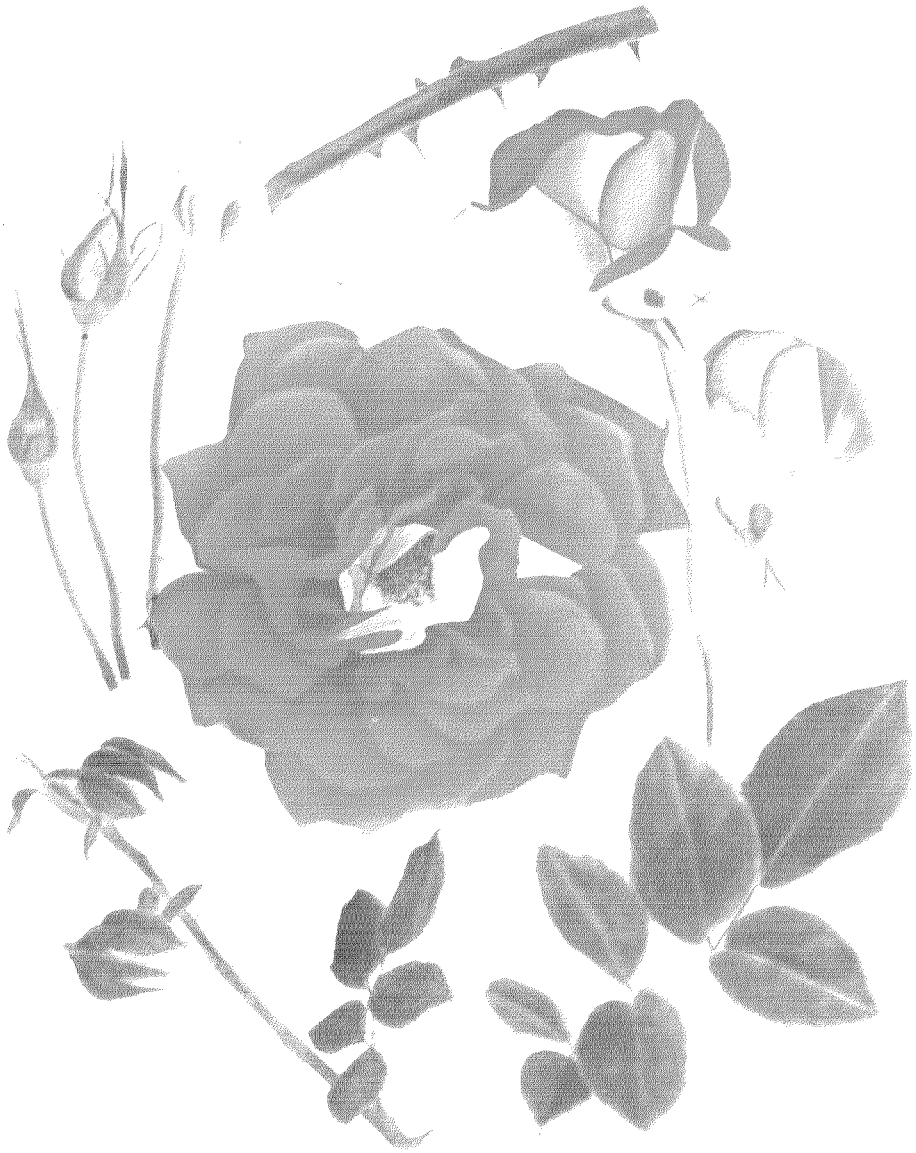
Inventor
E. S. Boerner
By Robert Robb
Attorneys Patented Feb. 16, 1954

Plant Pat. 1,252

UNITED STATES PATENT OFFICE 1,252

ROSE PLANT

Eugene S. Boerner, Newark, N. Y., assignor to Jackson & Perkins Company, Newark, N. Y., a corporation of New York Application February 24, 1953, Serial No. 338,629

1 Claim. (Cl. 47—61)

The present invention relates to a new and distinct variety of rose plant of the hybrid tea class, which was originated by me by crossing an unnamed and unpatented seedling of the hybrid tea variety "Lilette Mallerin" (unpatented) with an unnamed and unpatented seedling of the variety "Orange Nassau" (Plant Patent No. 350).

The primary objective of this cross was to produce a new variety of rose plant having blooms of the general color of the variety "Orange Nassau," but characterized by important improvements in the plant. Although the flower color of the variety "Orange Nassau" was not exactly achieved in my new variety, the red and yellow bi-color effect was preserved and retained, and has been combined with the characteristics of larger flowers, a more attractive combination of yellow, gold and red colors, and a more vigorous bush, thereby clearly distinguishing the new variety from its parents, as well as from all other varieties of its class.

Another unique and distinctive feature of my new variety is the peculiar misshapen petal form of the flowers, which usually occurs in the half-open bud, and which definitely distinguishes this new variety from its parents and from all others.

Asexual reproduction of the new variety by budding at Newark, New York, and at Pleasanton, California, shows that the foregoing characteristics and distinctions come true to form and are established and transmitted through succeeding propagations.

The accompanying drawing shows typical specimens of the flowers, stems and foliage of my new variety in different stages of development.

The following is a detailed description of my new variety, with color terminology in accordance with Ridgway's Color Standards and Nomenclature:

Parentage: Seedling.

*Seed parent.*—An unnamed hybrid tea seedling of the variety "Lilette Mallerin."

*Pollen parent.*—An unnamed seedling of the variety "Orange Nassau."

Classification:

*Botanic.*—Hybrid tea.

*Commercial.*—Hybrid tea.

*Flower*

(Observations made in a field at Newark, New York, in the early part of the month of July, late in the morning.)

Blooming habit: Recurrent; continuous.

Bud:

*Size.*—Large.

*Form.*—Ovoid; is not affected by wet or hot weather.

*Color.*—When sepals first divide—Clear Dull Green Yellow, Plate 17. When petals begin to unfurl—Pale Lemon Yellow, Plate 4. When half blown: inside of petals—Carmine, Plate 1, lightly overcast with Rose Red, Plate 12; reverse of petals—Lemon Chrome, Plate 4, with slight suffusion of Spectrum Red, Plate 1 on the outer edge of the petals.

*Sepals.*—Branched; "hood" above bud; curl back when petals begin to unfurl. Color: inside—Kildare Green, Plate 31; outside—Parrot Green, Plate 6.

*Calyx.* — Color — Parrot Green, Plate 6. Shape — apple. Size — broad. Aspect—smooth. Odor when rubbed—none.

*Peduncle.*—Length—long. Aspect — rough. Color—Lettuce Green, Plate 5. Strength—erect; heavy.

*Opening.*—Opens up well; is not affected by adverse weather conditions.

Bloom:

*Size.*—Large; average size when fully expanded—4½ inches to 5 inches.

*Borne.*—Singly.

*Stems.*—Long; strong.

*Form.*—When first open—high center. Permanence—flattening toward the end.

*Petalage.*—Double (full but open center). Number of petals under normal conditions—35 to 40.

*Color.*—Center of flower—Spectrum Red, Plate 1, lightly overcast with Rose Red, Plate 12. Outer petals—Rose Red, Plate 12, lightly overcast with Rose Color, Plate 12. Base of petals (aiglet)—Lemon Yellow, Plate 4. Inside of petals—Rose Red, Plate 12, lightly overcast with Begonia Rose, Plate 1 on the outer edges of the petals. Reverse of petals—Empire Yellow, Plate 4, with an overcast of Pale Lemon Yellow, Plate 4 in the lower half of the petal. General tonality from a distance—Spectrum Red, Plate 1.

*Discoloration.*—General tonality at end of first day—Spectrum Red, Plate 1. Second day—Rose Red, Plate 12, lightly overcast with Begonia Rose, Plate 1. Third day—Rose Red, Plate 12, lightly overcast with Rose Color, Plate 12.

Petals:

*Texture.*—Thick; is not affected by wet or hot weather.

*Appearance.* — Inside — satiny; outside—shiny.

*Form.*—Oval.

*Arrangement.* — Imbricated (regularly arranged shingle-like).

*Petaloids in center.*—Many; large.

*Persistence.*—Drop off cleanly.

*Fragrance.*—Moderate. Nature—tea (average hybrid tea scent).

*Lasting quality.*—On the plant and as cut flower—long.

*Genital organs*

Stamens, anthers: Large; many.

*Color.*—Deep Chrome, Plate 3.

*Arrangement.*—Regular around styles.

Stamens, filaments (threads): Long. Color—Mikado Orange, Plate 3.

Pollen: Color—Pale Orange-Yellow, Plate 3.

Styles: Bunched; uneven length; medium length; thin.

Stigmas: Color—Pale Yellow Orange, Plate 3.

Ovaries: All enclosed in calyx.

Seeds: None.

*Plant*

Form: Bush.

Growth: Vigorous; upright.

Foliage: 5 to 7 leaflets.

*Size.*—Large.

*Quantity.*—Normal abundance.

*Color.*—New foliage: upper side—Madder Brown, Plate 13; under side—Brownish Olive, Plate 30, lightly overcast with Madder Brown, Plate 13. Old foliage: upper side—Dark Dull Yellow Green, Plate 32; under side—Light Elm Green, Plate 17.

*Shape.*—Oval pointed.

*Texture.* — Upper side — leathery. Under side—smooth.

*Ribs and veins.*—Ordinary.

*Edge.*—Serrated (saw-toothed).

*Serration.*—Double and single; small.

*Leaf stem.*—Color—Hay's Russet, Plate 14. Underside—prickles.

*Stipules.*—Long; bearded.

Wood:

*New wood.*—Color—Cosse Green, Plate 5, lightly overcast with Hay's Russet, Plate 14. Bark—smooth.

*Old wood.*—Color—Dark Cress Green, Plate 31. Bark—smooth.

Thorns:

*Thorns.*—Quantity—on main stalks from base and on laterals from stalk—ordinary. Form—flat base; straight and hooked downward. Color when young—Kildare Green, Plate 31. Position—irregular.

*Prickles.*—Quantity—on main stalks and on laterals—none.

*Short needles.*—Quantity—on main stalks and on laterals—none.

I claim:

A new and distinct variety of rose plant of the hybrid tea class and bi-color type, substantially as herein shown and described, characterized particularly as to novelty by the vigorous habit of the plant, and by the sharp combination of yellow and gold colors of the petals as they appear before the flowers open, changing to red as the flowers open to full bloom, by the relatively large size of the flowers, and by the peculiar misshapen petal form which usually occurs in the half-open bud.

EUGENE S. BOERNER.

No references cited.